United States Patent [19]

Schein

[11] Patent Number: 5,804,571

[45] Date of Patent: Sep. 8, 1998

[54] METHOD FOR PROTECTION FROM AZT SIDE EFFECTS AND TOXICITY

[75] Inventor: Philip S. Schein, Bryn Mawr, Pa.

[73] Assignee: U.S. Bioscience, Blue Bell, Pa.

[21] Appl. No.: 486,625

[22] Filed: Jun. 7, 1995

Related U.S. Application Data

[63] Continuation of Ser. No. 308,220, Sep. 19, 1994, abandoned, which is a continuation of Ser. No. 162,792, Dec. 7, 1993, abandoned, which is a continuation of Ser. No. 936,334, Aug. 28, 1992, abandoned, which is a continuation of Ser. No. 356,298, May 24, 1989, abandoned.

[51] Int. Cl.$^6$ ........................... A61K 31/70; A61K 31/66
[52] U.S. Cl. ........................... 514/114; 514/50; 514/922; 424/406
[58] Field of Search ............................. 514/114, 50, 922; 424/406

[56] References Cited

U.S. PATENT DOCUMENTS 3,892,824  7/1975  Piper et al. ............................. 514/917
4,874,602  10/1989  Calabresi et al. ........................ 514/50

OTHER PUBLICATIONS

The Effects of Radiation: How Much Radiation Does it Take to Cause Cancer? In Dimensions of Cancer by C.E. Kupchella p. 151, 1987, Wadsworth Publishing Co.

*Primary Examiner*—Gollamudi S. Kishore
*Attorney, Agent, or Firm*—Merchant, Gould, Smith, Edell, Welter & Schmidt, P.A.

[57] ABSTRACT

S-ω(ω-aminoalkylamino)alkyl dihydrogen phosphorothioates or pharmaceutically acceptable derivatives thereof are useful in protecting a patient undergoing AZT treatment for AIDS and AIDS-related complex from the harmful side effects or reactions and toxicity of the AZT.

8 Claims, No Drawings

METHOD FOR PROTECTION FROM AZT SIDE EFFECTS AND TOXICITY

This is a continuation of application Ser. No. 08/308,220 filed Sep. 19, 1994, now abandoned, which is a continuation of application Ser. No. 08/162,792, filed on Dec. 7, 1993, now abandoned which is a continuation of Ser. No. 07/936,334, filed Aug. 28, 1992, which is a continuation of Ser. No. 07/356,298, filed May 24, 1989 now abandoned.

BACKGROUND OF INVENTION

Drug treatment for the human immunodeficiency virus (HIV), the etiologic agent of the acquired immunodeficiency syndrome (AIDS) and AIDS-related complex, includes azidothymidine (3'-azido-3'-deoxythymidine; zidovudine [Retrovir], or AZT). While clinical benefits with AIDS have been reported, New England Journal of Medicine, 1987; 317:185–91, serious adverse reactions, particularly bone marrow suppression were observed. In a study of the toxicity of AZT in the treatment of AIDS patients, nausea, myalgia, insomnia, and severe headaches were reported more frequently by recipients of AZT when compared to those given a placebo; macrocytosis developed within weeks in most of the AZT group of patients; anemia with hemoglobin levels below 7.5 per deciliter developed in 24 percent of AZT recipients and 4 percent of placebo recipients (P less than 0.001); 21 percent of AZT recipients and 4 percent of placebo recipients required multiple red-cell transfusions (P less than 0.001); neutropenia (less than 500 cells per cubic millimeter) occurred in 16 percent of AZT recipients as compared with 2 percent of placebo recipients (P less than 0.001), New England Journal of Medicine, 1987; 317:192–97.

The HIV virus depresses the human immune system, leaving the AIDS patient vulnerable to diseases that would otherwise not ordinarily be considered fatal. Consequently, AZT can not be administered in amounts that further suppress the patient's immune system and resistance to disease. Often anemia becomes an important health problem and a patient will often need multiple blood transfusions. Moreover, it has been recently observed that some strains of HIV may be resistant to AZT and higher AZT dosages are necessary to be effective.

The present invention is directed towards decreasing the toxicity and adverse reactions in AIDS or AIDS-related complex patients being treated with AZT without significant damage to the beneficial therapeutic benefits of the AZT.

SUMMARY OF INVENTION

The present invention involves a method for decreasing the toxicity and the adverse reactions associated with the treatment of AIDS and AIDS-related complex patients being treated with AZT through oral and intravenous administration of S-ω(ω-amino-alkylamino) alkyl dihydrogen phosphorothioates, particularly S-2-(3-aminopropylamino) ethyl dihydrogen phosphorothioate and S-3-(3-methylaminopropylamino)propyl dihydrogen phosphorothioate or derivatives thereof.

DETAILED DESCRIPTION OF THE INVENTION

The present invention is directed toward a method of decreasing the side effects or reactions and toxicity of AZT administered in AIDS and AIDS-related complex treatment comprising oral or intravenous administration to a patient undergoing said treatment with effective amounts of S-ω(ω-aminoalkylamino) alkyl dihydrogen phosphorothioates, particularly S-3-(3-methylaminopropylamino)propyl dihydrogen phosphorothioate and S-2-(3-aminopropylamino)ethyl dihydrogen phosphorothioate and pharmaceutically acceptable salts or hydrates thereof.

Oral administration of the phosphorothioate is particularly desirable. By oral administration, there is contemplated preparation of the phosphorothioate in any dosage form capable of oral administration. Such dosage forms include tablets, capsules, caplets, solutions and the like. S-3-(3-methylamino-propylamino)propyl dihydrogen phosphorothioate and salts or hydrates thereof are particularly useful oral agents. The oral dosage form is administered from 0–60 minutes, preferably 15 minutes, before the azidothymidine is administered to the patient.

As an effective amount of the compounds of the present invention, administered orally, there is contemplated any amount which would serve to decrease the side effects or reactions and the toxicity of the azidothymidine. For example, a dosage of between about 200 mg–2 g/m$^2$ body surface area of the patient is contemplated, with a total dosage of up to 8 g/m$^2$ body surface area of the patient per day being administered. A preferred dosage is 1 g/m$^2$ body surface area of the patient every six hours.

The oral dosage forms of the present invention may contain pharmaceutically acceptable inert ingredients. As such inert ingredients there are contemplated pharmaceutical carriers, excipients, fillers, etc. which do not interfere with the activity of the compound. Also, fillers such as clays or siliceous earth may be utilized if desired to adjust the size of the dosage form.

Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, caroboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

Also in accordance with the present invention, there is provided a liquid-based dosage form suitable for the administration of the composition to a patient. The liquid base for this dosage form may be any liquid capable of transporting the composition into the body of a patient without disrupting the activity of the compound or harm the patient. Exemplary of such a liquid is an isotonic solution. The isotonic solution may also contain conventional additives therein such as sugars. These solutions can be used in the preparation of oral and intravenous compositions.

When the phosphorothioate is administered intravenously, particularly preferred is drip intravenous infusion in a buffered aqueous solution 15 to 30 minutes before administration of the azidothymidine agent. S-2-(3-aminopropylamino)ethyl dihydrogen phosphorothioate is a particularly useful intravenous agent.

Thus, the compositions of the present invention may be admixed according to known procedures using known excipients.

As an effective amount of the compounds of the present invention, administered intravenously, there is contemplated any amount which would serve to decrease the side effects or reactions and the toxicity of the azidothymidine. For example, a dosage of between about 50 to about 2500 mg/m$^2$ body surface area of the patient is contemplated. A preferred dosage according to the present invention is from about 300 to about 1000 mg/m$^2$ body surface area of the patient, with a most preferred dosage of 740 mg/m$^2$ body surface area of the patient. The active ingredient may be administered in single or divided doses.

S-ω(ω-aminoalkylamino)alkyl dihydrogen phosphorothioates can be depicted as follows:

RNH($C_nH_{2n}$)NH($C_nH_{2n}$)SPO$_3$H$_2$ wherein R is hydrogen or an alkyl group containing 1 to 7 carbon atoms and each n independently has a value of from 2 to 6. Pharmaceutically acceptable derivative such as hydrates and alkali metal salts are contemplated as being within the scope of this invention. Such compounds are disclosed in U.S. Pat. No. 3,892,824 to Piper et al., the disclosure of which is incorporated by reference.

S-3-(3-methylaminopropylamino)propyl dihydrogen phosphorothioate can be depicted as follows:

CH$_3$—NH—(CH$_2$)$_3$—NH—(CH$_2$)$_3$—S—PO$_3$H$_2$.

S-2-(3-aminopropylamino)ethyl dihydrogen phosphorothioate can be depicted as follows:

NH$_2$—(CH$_2$)$_3$—NH—(CH$_2$)$_2$—SPO$_3$H$_2$.

EXAMPLES

Illustrative examples of the present invention follow.

Example I

S-2-(3-aminopropylamino)ethyl dihydrogen phosphorothioate monohydrate may be prepared in accordance with the following procedure:

A solution of 2-(3-aminopropylamino)ethanol (25.0 g, 0.212 mole) in 48 percent hydrobromic acid (200 ml) was distilled until 35 ml of distillate had been collected. The solution was refluxed and, periodically, more distillate was collected. The total volume of distillate removed in seven distillation periods was 160 ml, or 80 percent of the original volume of 48 percent hydrobromic acid, and the time of continuous boiling was approximately 48 hours. The residual solution was then evaporated to dryness under reduced pressure with the aid of several added portions of methanol. The crystalline residue was thoroughly triturated with acetone, collected, and washed on the funnel with acetone. After the product had been pressed as dry as possible on the funnel, it was dissolved in a slight excess of boiling methanol and the solution was filtered. Addition of acetone to the filtrate precipitated pure N-(2-bromoethyl)-1,3-propanediamine dihydrobromide as colorless crystals, which were dried in vacuo over phosphorus pentoxide; yield 58.0 g (80%), mp 205°–206° C.

Trisodium phosphorothioate (6.93 g, 38.5 mmoles) was gradually added in small portions with vigorous stirring to water (38 ml) cooled externally be means of a water bath (15°–20° C.). To the resulting suspension was added N-(2-bromoethyl)-1,3-propanediamine dihydrobromide (13.3 g, 38.8 mmoles). After a few minutes, complete solution occurred, and N,N-dimethylformamide (19 ml) was added with continued external cooling at 15°–20° C.

After the solution had been stirred at about 20° C. for 90 minutes, it was poured into methanol (250 ml), and the mixture was refrigerated at 4° C. overnight. The white precipitate that formed was collected and pressed as dry as possible on the funnel. The same solid was dissolved in water (40 ml), and the solution was filtered. Addition of methanol (250 ml) reprecipitated the product. After the mixture had been refrigerated about 1 hour, the product was collected and washed on the funnel, first with methanol and finally with ether. The white solid was dried in vacuo at room temperature, then exposed to ambient conditions of the laboratory for 5 hours, and bottled under nitrogen and stored in a freezer. The yield of S-2-(3-aminopropylamino)ethyl dihydrogen phosphorothioate monohydrate, mp 160°–161° C. dec. was 8.15 g (91%). Anal. Calcd. for C$_3$H$_{13}$N$_2$O$_3$PS.H$_2$O: C, 25.86; H, 7.38; N, 12.07. Found: C, 25.83; H, 7.27; N, 11.81.

Example II

S-3-(3-methylaminopropylamino)propyl dihydrogen phosphorothioate may be prepared in accordance with the following procedure:

Preparation of N-Methyl-N,N'-trimethylenebis-p-toluenesulfonamide (1). —A freshly prepared solution of p-toluenesulfonyl chloride (90.8 g, 0.476 mole) in N,N-dimethylformamide (200 ml) is added during 45 min. with moderate external cooling to a stirred solution of N-methyl-1,3-propanediamine (41.9 g, 0.476 mole) in N,N-dimethylformamide (150 ml) at such a rate that the temperature does not exceed 40° C. The mixture is stirred 45 min. longer at room temperature and then poured into cold water (1.2 l.). The white gum that precipitated, solidifies on standing. The crude product is collected, pulverized, and washed thoroughly with water. Recrystallization from ethanol affords the pure product, m.p. 93° C. (Kofler Heizbank), in 79% yield (74.4 g).

Anal. Calcd. for C$_{18}$H$_{24}$N$_2$O$_4$S$_2$: C, 54.52; H, 6.10; S, 16.17 Found: C, 54.33; H, 5.92; S, 16.4.

Preparation of 3-Chloropropyl Acetate (2). —Acetic anhydride (114 g, 1.12 mole) is added in a thin stream to a stirred mixture of 3-chloro-l-propanol (94.5 g, 1.00 mole) and glacial HOAc (50 ml). The solution is refluxed 2 hours, cooled, and poured into H$_2$O (200 ml). The layers are separated, and the aqueous layer is thoroughly extracted with Et$_2$O (five times with 100-ml portions). The original organic layer is then combined with the Et$_2$O solution, and the resultant solution is washed several times with H$_2$O followed by saturated NaHCO$_3$ solution and finally with H$_2$O. The dried (MgSO$_4$) solution is fractionally distilled under reduced pressure to give 2, bp 63°–66° C. (12–14 mm) [G. M. Bennett and F. Heathcoat, J. Chem. Soc., 268 (1929). bp 66° C. (14 mm)], in 80% yield (109 g).

Preparation of Trisodium phosphorothioate. —Thiophosphoryl chloride (56.5 g, 0.333 mole) is added to a solution of sodium hydroxide (80.0 g, 2.00 moles in 500 ml of water), and the mixture is heated with vigorous magnetic stirring to 83°–84° C. The heat source (Glas-Col mantle) is then immediately removed, and the mixture is quickly cooled to 75°–77° C. by means of a water bath. When the water bath is removed, the temperature of the vigorously stirred mixture gradually rises spontaneously. The temperature is allowed to rise to 83°–84° C., and the mixture is again cooled rapidly back to 75°–77° C. This process of alternately cooling and allowing spontaneous temperature rise is repeated about six times, or until so little unreacted thiophosphoryl chloride remains that the spontaneous rise in temperature no longer occurs. The mixture, which is yellow in color, is then heated at 82-84° C with continued stirring until the oily droplets of thiophosphoryl chloride disappear. [The total reaction period required is about 1 hr. As short a reaction time as possible is desired.]

Immediately after the mixture becomes clear, it is chilled rapidly in an ice-water bath to about 4° C. The crystalline hydrated form of the product commences precipitating when the solution becomes cold. The mixture is then allowed to stand in the refrigerator at 4° C. for about 16 hours. The crystalline precipitate is collected with the aid of the cold filtrate, pressed as dry as possible on the funnel, and washed with absolute ethanol (100 ml). The precipitate is then removed from the funnel and dissolved in water (250 ml) at 45° C. The solution is filtered immediately. Absolute ethanol (200 ml) is gradually added with swirling to the filtrate, and the mixture is then cooled in a cold water bath to about 20° C. The reprecipitated product is collected and washed with ethanol (100 ml). The product is then dehydrated by adding it to dry methanol (600 ml) and stirring the resultant mixture under anhydrous conditions for 1.5 hr. The white methanol-insoluble solid is collected and dried for approximately 30 min. at 100° C. in vacuo over phosphorus pentoxide. The anhydrous trisodium phosphorothioate thus obtained is a white powder amounting to about 50 g (83% yield), and should be stored in a freezer under anhydrous conditions.

Preparation of N-(2-Acetoxyethyl)-N'-Methyltrimethylenebis-p-Toluenesulfonamide (3). A solution of (1) (39.5 g, 0.100 mole) in N,N-dimethylformamide (12.5 ml) is added during 1 hr. to a stirred suspension of sodium hydride (4.00 g of 60% oil dispersion, 0.100 mole of NaH) in N,N-dimethylformamide (75 ml) with moderate external cooling to maintain the temperature at about 30° C. The mixture is stirred 1 hr. longer at room temperature, and a virtually clear solution results.

Freshly distilled (2) is added (13.5 g, 0.100 mole), and the resultant mixture is left to stir 42 hours at room temperature. The mixture is then heated at 80°–85° C. for 2 hours. Most of the solvent is removed by distillation in vacuo, and the residual red-orange syrup is dissolved in benzene (250 ml). The benzene solution is washed with water (4×50 ml) and dried ($NaSO_4$). Removal of the benzene by evaporation under reduced pressure leaves an orange oil that is used as such.

Preparation of N-(3-Bromopropyl)-N'-Methyl-1,3-Propanediamine Dihydrobromide (4). —A stirred mixture of crude 3 described above (46.5 g) and 48 percent HBr (500 ml) is refluxed overnight and then slowly distilled through a 30 cm Vigreux column until 300 ml of distillate is collected during 8 hours. The solution that remained is cooled, treated with Norit, filter (Celite), and evaporated to dryness with aid of added portions of MeOH (aspirator, rotary evaporator, bath up to 70° C.). The residue is recrystallized successively from MeOH (Norit)-$Et_2$ O and MeOH to give pure 4, mp 220°–222° C. dec., in 40% yield (13.8 g), Anal. Calcd. for $C_7H_{19}$ $BrN_2$ 2HBr: C, 22.66; H, 5.16; Br, 64.62; N, 7.55. Found: C, 22.69; H, 5.22; Br, 64.48; N, 7.68.

Preparation of S-3-(3-Methylaminopropylamino)propyl Dihydrogen Phosphorothioate (5) Trihydrate. —Solid (4) (7.80 g, 21.0 mmol) is added in portions to a stirred partial solution of $Na_3$ $SPO_3$ (3.60 g, 20.0 mmol) in $H_2O$ (20 ml). The mixture, which soon becomes clear, is stirred at 25°–30° C. for 1.75 hr, poured into DMF (80 ml), and refrigerated overnight. The precipitate is collected, dissolved in $H_2O$ (20 ml), and reprecipitated by addition of EtOH. The crystalline product is collected with the aid of EtOH, washed successively with EtOH followed by $Et_2O$, air dried, and then equilibrated at constant 50% relative humidity to give pure (5)$3H_2O$, mp 115°–120° C., in 85% yield (5.04 g). Anal. Calcd. for $C_7H_{19}N_2O_3$ $PS.3H_2O$: C, 28.37; H, 8.50; N, 9.45; P, 10.45; P, 10.45; S, 10.82. Found: C, 28.35; H, 8.32; N, 9.48; P, 10.57; S, 10.91.

Preparation of 3-(3-methylaminopropylamino) propanethiol dihydrochloride (6). —The preparation of (5) described above is repeated (21.6 mmol of 4, 20.6 mmol of $Na_3SPO_3$), and the reprecipitated product (from $H_2O$-EtOH) is used for conversion to (6) without further characterization. The sample is dissolved in 3N HCl (30 ml), and the solution is heated in a boiling $H_2O$ bath for 10 min. The cooled solution is diluted with EtOH (300 ml), and $Et_2$ O (200 ml) is added. The cloudy mixture is refrigerated overnight while crystalline solid separates. This material, collected under $N_2$ and suction dried under $N_2$ pressure is dissolved in MeOH (100 ml), and EtOH (500 ml) is added followed by a solution of dry HCl in EtOH (3 N, 25 ml). Crystalline (6), which separates readily, is collected under $N_2$, washed with EtOH followed by $Et_2O$, and dried in vacuo (25°–30° C., $P_2O_5$); the overall yield was 58% (2.80 g), mp 244°–246° C. dec. Anal. Calcd. for $C_7H_8N_2S.2HCl$: C, 35.74; H, 8.57; N, 11.91; S, 13.63; SH, 14.06. Found: C, 35.59; H, 8.69; N, 11.86; S, 13.44; SH, 14.28.

Example III

To evaluate toxicity to the murine hematopoietic system, an exogenous spleen colony (CFU-S) assay was used. A suitable number of murine bone cells are injected (intravenously) into lethally irradiated syngeneic mice (Ref. Hodgson, G. S., and Bradley, T. R., *Properties of Haematopoietic Stem Cells Surviving* 5-FU Treatment: Evidence for a pre-CFU-S Cell48, Nature 281:381, 1979).

Colonies are found in the spleen of the recipients on Day 9 or 10; there is a linear relationship between the number of cells injected and the number of spleen colonies. The spleen colonies originate from a single cell, and contain cells of the erythroid, granulocytic and megakaryocytic series.

S-3-(3-methylaminopropylamino)propyl dihydrogen phosphorothioate [dissolved at 4° C. in Lactated Ringer's and 5% Dextrose, pH adjusted to 7.2–7.3 with sodium bicarbonate, immediately prior to use] was administered at 900 mg/kg orally followed within 30 minutes with AZT (dissolved in sterile water prior to use at 20 mgAZT/ml) at 400 mg/kg intraperitoneally.

At 20 hours after drug administration, each mouse was sacrificed and bone marrow was extracted from the femurs into McCoy's 5A medium (GIBCOm Grand Island, N.Y.) on ice. Nucleated marrow cells were quantitated, and 5×104 cells were injected intravenously into syngeneic recipient mice one hour after they received 800 rads whole body radiation. Nine days later, the recipient animals were sacrificed, and the spleens were removed and fixed in Boulin's solution. Surface colonies were then counted.

| Drug Treatrnent | Time of CFU-S Assay (hours after drug administration) | CFU-S Survival (% of Control) |
|---|---|---|
| S-3-(3-methylamino propylamino) propyl dihydrogen phosphorothioate at 900 mg/kg po, followed in 30 minutes with AZT, 400 mg/kg ip | 20 hrs | 68% |
| AZT, 400 mg/kg ip | 20 hrs | 18% |

Example IV 1000 mg of S-3-(3-methylaminopropylamino)propyl dihydrogen phosphorothioate is suspended in an isotonic solution. 200 mg/m² body surface area of S-3-(3- methylaminopropylamino)propyl dihydrogen phosphorothioate thus suspended is administered intravenously to a patient undergoing treatment with AZT 20 minutes before administration of AZT.

Example V 500 mg of S-3-(3-methylaminopropylamino)propyl dihydrogen phosphorothioate is suspended in an isotonic solution. 500 mg/m$^2$ body surface area of S-3-(3-methylaminopropylamino)propyl dihydrogen phosphorothioate thus suspended is administered to a patient undergoing treatment with AZT 25 minutes before administration of AZT.

Example VI 1000 mg of S-3-(3-methylaminopropylamino)propyl dihydrogen phosphorothioate is admixed with hydroxypropylcellulose and stearyl alcohol. The mixture is then compressed into tablet form. 200 mg/m$^2$ body surface area of S-3-(3-methylaminopropyl-amino) propyl dihydrogen phosphorothioate thus prepared is administered orally to a patient undergoing treatment with AZT, 15 minutes before administration of AZT.

Example VII 700 mg of S-3-(3-methylaminopropylamino)propyl dihydrogen phosphorothioate is admixed with hydroxypropylcellulose and glycowax. The mixture is then compressed into tablet form. 500 mg/m$^2$ body surface area of S-3-(3-methylaminopropylamino) propyl dihydrogen phosphorothioate thus prepared is administered orally to a patient undergoing treatment with AZT, 25 minutes before administration of AZT.

Example VIII 1000 mg of S-3-(3-methylaminopropylamino)propyl dihydrogen phosphorothioate is admixed with hydroxypropylcellulose and stearyl alcohol. The mixture is then compressed into tablet form. 200 mg/m$^2$ body surface area of S-3-(3-methylaminopropyl-amino) propyl dihydrogen phosphorothioate thus prepared is administered orally to a patient undergoing treatment with AZT, 45 minutes before administration of AZT.

Example IX

The S-2-(3-aminopropylamino)ethyl dihydrogen phosphorothioate can be stored frozen at low temperatures, e.g., negative 70° C. The I.V. carrier solution may be a buffered solution of 5% dextrose in Ringers lactate, having a pH of about 7.2 to 7.4. This solution can be made by adding 20 cc of 44.9 mEq sodium bicarbonate to 1 liter of 5% dextrose in Ringers lactate. 9.3 cc of the solution can be added to vial containing 500 mg of S-2-(3-aminopropylamino)ethyl dihydrogen phosphorothioate to produce a solution containing 50 mg/cc of S-2-(3-aminopropylamino)ethyl dihydrogen phosphorothioate. Prior to administration, further buffered solution can be added for a total volume of 50 cc, and the resulting solution can be administered to a patient undergoing treatment with AZT over a period of about 15 minutes, using a volumetric pump.

What is claimed is:

1. A method for treating a patient undergoing treatment for the human immunodeficiency virus, comprising administration to the patient of azidothymidine and an amount of a S-ω(ω-aminoalkylamino)-alkyl dihydrogen phosphorothioate, or a pharmaceutically acceptable salt or hydrate thereof, effective to protect the patient from at least one undesired side effect of the azidothymidine selected from the group consisting of nausea, myalgia, insomnia, headache, anemia, and neutropenia.

2. The method of claim 1, wherein the S-ω(ω-aminoalkylamino)alkyl dihydrogen phosphorothioate or salt or hydrate thereof is administered orally.

3. The method of claim 1, wherein the S-ω(ω-aminoalkylamino)alkyl dihydrogen phosphorothioate or salt or hydrate thereof is administered about 15 to 30 minutes before administration of the said azidothymidine.

4. The method of claim 1, wherein the amount of S-ω(ω-aminoalkylamino)alkyl dihydrogen phosphorothioate or salt or hydrate thereof is an amount not greater than 2,500 mg/m$^2$ of body surface area of patient.

5. The method of claim 4, wherein the amount of S-ω(ω-aminoalkylamino)alkyl dihydrogen phosphorothioate or salt or hydrate thereof is about 300 to 1,000 mg/m$^2$ of body surface area of patient.

6. The method of claim 5, wherein the amount of S-ω(ω-aminoalkylamino)alkyl dihydrogen phosphorothioate or salt or hydrate thereof is about 740 mg/m$^2$.

7. The method of claim 1, wherein S-2-(3-aminopropylamino)ethyl dihydrogen phosphorothioate or salt or hydrate thereof is administered via drip intravenous infusion in a buffered aqueous solution.

8. The method of claim 2, wherein S-3-(3-methylaminopropylamino)propyl dihydrogen phosphorothioate or salt or hydrate thereof is administered orally.

* * * * *